United States Patent
Jawidzik

(10) Patent No.: US 11,740,648 B2
(45) Date of Patent: Aug. 29, 2023

(54) SURGICAL FOOTSWITCH HAVING ELEVATED AUXILIARY BUTTONS

(71) Applicant: Alcon Inc., Fribourg (CH)

(72) Inventor: Geoffrey C. Jawidzik, Mission Viejo, CA (US)

(73) Assignee: Alcon Inc., Fribourg (CH)

( * ) Notice: Subject to any disclaimer, the term of this patent is extended or adjusted under 35 U.S.C. 154(b) by 42 days.

(21) Appl. No.: 16/931,532

(22) Filed: Jul. 17, 2020

(65) Prior Publication Data

US 2021/0035747 A1 Feb. 4, 2021

Related U.S. Application Data

(60) Provisional application No. 62/881,662, filed on Aug. 1, 2019.

(51) Int. Cl.
*G05G 1/30* (2008.04)
*H01H 3/14* (2006.01)
*A61B 17/00* (2006.01)

(52) U.S. Cl.
CPC ............. *G05G 1/305* (2013.01); *H01H 3/14* (2013.01); *A61B 2017/00973* (2013.01)

(58) Field of Classification Search
CPC . G05G 1/30; G05G 1/305; G05G 1/44; A61B 2017/00199; A61B 2017/00973; H01H 3/14; H01H 13/16; H01H 21/26
See application file for complete search history.

(56) References Cited

U.S. PATENT DOCUMENTS

| | | | | | |
|---|---|---|---|---|---|
| 3,427,583 | A | * | 2/1969 | Zackey | H01H 21/26 340/464 |
| 5,554,894 | A | * | 9/1996 | Sepielli | G05G 1/44 307/119 |
| 5,787,760 | A | * | 8/1998 | Thorlakson | G05G 1/30 200/86.5 |
| 6,150,623 | A | * | 11/2000 | Chen | A61F 9/008 74/478 |

(Continued)

FOREIGN PATENT DOCUMENTS

| | | | | |
|---|---|---|---|---|
| AU | 2015203096 B2 | * | 9/2016 | |
| JP | 2011206596 A | * | 10/2011 | ............. A61B 17/00 |
| KR | 20040021558 A | * | 3/2004 | |

*Primary Examiner* — Adam D Rogers
(74) *Attorney, Agent, or Firm* — Patterson + Sheridan, LLP

(57) ABSTRACT

A surgical footswitch having elevated auxiliary buttons is provided. In particular embodiments, the surgical footswitch comprises a footswitch base, a treadle mounted on the footswitch base, a first primary button positioned on an upper surface of the footswitch base along a first lateral side of the treadle, a first auxiliary button housing positioned along a lateral side of the first primary button opposite the treadle, and a first auxiliary button mounted on an upper surface of the first auxiliary button housing, wherein an upper surface of the first auxiliary button is elevated in relation to an upper surface of the first primary button. In particular embodiments, the treadle is configured to activate a first function of a surgical console, the first primary button is configured to activate a second function of the surgical console, and the first auxiliary button is configured to activate a third function of the surgical console.

20 Claims, 5 Drawing Sheets

(56) References Cited

U.S. PATENT DOCUMENTS

| | | | | |
|---|---|---|---|---|
| 6,179,829 B1 | * | 1/2001 | Bisch | A61C 1/0023 606/1 |
| 6,452,120 B1 | * | 9/2002 | Chen | G05G 1/30 200/86.5 |
| D478,323 S | * | 8/2003 | Peterson | D13/167 |
| 6,659,998 B2 | | 12/2003 | Dehoogh et al. | |
| 6,689,975 B2 | * | 2/2004 | Metzler | A61F 9/00 200/334 |
| 6,862,951 B2 | * | 3/2005 | Peterson | G05G 1/30 74/512 |
| 6,962,581 B2 | * | 11/2005 | Thoe | A61B 17/00 200/51.02 |
| 7,012,203 B2 | * | 3/2006 | Hanson | A61B 17/00 200/86.5 |
| 7,019,234 B1 | | 3/2006 | Mezhinsky | |
| 7,084,364 B2 | | 8/2006 | Mezhinsky | |
| 7,185,555 B2 | | 3/2007 | Peterson | |
| 7,193,169 B2 | | 3/2007 | Mezhinsky | |
| 7,381,917 B2 | * | 6/2008 | Dacquay | H01H 3/14 200/86.5 |
| 7,470,277 B2 | * | 12/2008 | Finlay | A61B 17/00 200/86.5 |
| 7,619,171 B2 | | 11/2009 | Horvath | |
| 7,626,132 B2 | * | 12/2009 | Mezhinsky | A61F 9/00736 200/86.5 |
| 7,781,941 B2 | | 8/2010 | Horvath | |
| 8,048,094 B2 | | 11/2011 | Finlay | |
| D669,441 S | * | 10/2012 | Naef | D13/167 |
| 8,465,473 B2 | | 6/2013 | Horvath | |
| 8,749,188 B2 | * | 6/2014 | Tran | A61B 34/25 318/545 |
| D727,498 S | * | 4/2015 | Creed | D24/144 |
| D743,036 S | | 11/2015 | Boukhny et al. | |
| 9,240,110 B2 | * | 1/2016 | Roth | H01H 3/14 |
| 10,058,450 B2 | * | 8/2018 | Hajishah | A61F 9/007 |
| 10,243,557 B2 | | 3/2019 | Ekvall | |
| 10,736,700 B2 | | 8/2020 | Mercado | |
| 10,747,255 B2 | * | 8/2020 | Gahler | A61F 9/00736 |
| 10,828,193 B2 | * | 11/2020 | Lynn | A61F 9/00745 |
| 10,864,054 B2 | | 12/2020 | Jochinsen et al. | |
| 10,901,450 B2 | * | 1/2021 | Jawidzik | G05G 1/44 |
| 10,925,680 B2 | * | 2/2021 | Jawidzik | A61B 34/25 |
| D911,982 S | * | 3/2021 | Colter | D13/167 |
| 2004/0036386 A1 | * | 2/2004 | Olivera | A61B 50/10 312/209 |
| 2007/0149956 A1 | * | 6/2007 | Liedel | A61F 9/00804 606/4 |
| 2008/0114387 A1 | * | 5/2008 | Hertweck | A61F 9/00745 606/170 |
| 2010/0198200 A1 | * | 8/2010 | Horvath | G05G 1/305 606/1 |
| 2012/0083800 A1 | * | 4/2012 | Andersohn | A61F 9/00736 606/130 |
| 2015/0173725 A1 | | 6/2015 | Maxson | |
| 2019/0125182 A1 | | 5/2019 | Charles | |
| 2019/0354200 A1 | | 11/2019 | Rapoport | |
| 2021/0137595 A1 | * | 5/2021 | Jawidzik | G01V 8/20 |
| 2021/0386412 A1 | * | 12/2021 | Colter | A61F 9/00745 |
| 2022/0273275 A1 | * | 9/2022 | Dam-Huisman | H01H 3/14 |

* cited by examiner

SURGICAL FOOTSWITCH HAVING ELEVATED AUXILIARY BUTTONS

PRIORITY CLAIM

This application claims the benefit of priority of U.S. Provisional Patent Application Ser. No. 62/881,662 titled "Surgical Footswitch Having Elevated Auxilary Buttons", filed on Aug. 1, 2019, whose inventor is Geoffrey C. Jawidzik, which is hereby incorporated by reference in its entirety as though fully and completely set forth herein.

TECHNICAL FIELD

This disclosure relates to the field of surgical consoles and, more particularly, to a surgical footswitch having elevated auxiliary buttons.

BACKGROUND

Surgical consoles are used in modern surgery, particularly ophthalmic surgery, to perform a variety of surgical tasks. Oftentimes this involves using the surgical console to power and control a variety of pneumatically and/or electrically driven handheld instruments used by the surgeon during the procedure. Because these handheld instruments often occupy both of a surgeon's hands, other forms of operating the console have been developed. Surgical footswitches provide one such form of controlling the console. However, because the surgeon is often fully engaged with a microscope or display unit during surgery, a surgeon must be able to operate the footswitch with minimum visual interaction. Moreover, as surgical consoles have become increasingly complex and added additional functionalities, there has been a push to be able to control more of these additional functionalities using footswitches. Oftentimes this involves adding additional buttons to the footswitch. However, as additional buttons are added to a surgical footswitch, it increases the risk that a user will inadvertently activate one button when attempting to activate another one, especially when the user does not look at the footswitch during the procedure.

BRIEF SUMMARY

In accordance with the teachings of the present disclosure, a surgical footswitch comprising at least one elevated, auxiliary button is disclosed. In a particular embodiment, the surgical footswitch comprises a footswitch base, a treadle mounted on the footswitch base, a first primary button positioned on an upper surface of the footswitch base along a first lateral side of the treadle, a first auxiliary button housing positioned along a lateral side of the first primary button opposite the treadle, and a first auxiliary button mounted on an upper surface of the first auxiliary button housing, wherein an upper surface of the first auxiliary button is elevated in relation to an upper surface of the first primary button.

In another embodiment, the surgical footswitch comprises a footswitch base, a treadle mounted on the footswitch base, a first primary button positioned on an upper surface of the footswitch base along a first lateral side of the treadle, and a second primary button positioned on the upper surface of the footswitch base along a second lateral side of the treadle. The exemplary footswitch further comprises a first auxiliary button housing positioned along a lateral side of the first primary button opposite the treadle, a first auxiliary button mounted on an upper surface of the first auxiliary button housing, a second auxiliary button housing positioned along a lateral side of the second primary button opposite the treadle, and a second primary button mounted on an upper surface of the second auxiliary button housing. An upper surface of the first auxiliary button may be elevated in relation to an upper surface of the first primary button, and an upper surface of the second auxiliary button may be elevated in relation to an upper surface of the second primary button.

By providing one or more elevated, auxiliary buttons, particular embodiments of the present disclosure are able to provide users with a surgical footswitch that offers enhanced functionality. For example, a user may be able to select between more functions, or combinations of functions, due to the addition of the auxiliary buttons, without removing his or her foot from the treadle. Moreover, by elevating the auxiliary buttons relative to the primary buttons, particular embodiments may help reduce the risk that the user will inadvertently activate the auxiliary buttons when attempting to activate the primary buttons and/or treadle of the footswitch. Similarly, particular embodiments may also help to reduce the risk that the user will inadvertently activate the primary buttons and/or treadle when attempting to activate the auxiliary buttons. And, by placing the auxiliary buttons such that there is a significant difference in the vertical and/or horizontal placement of the auxiliary and primary buttons, particular embodiments may better enable the user to activate the buttons without having to view the footswitch, allowing the user to maintain his or her vision on the surgical field.

BRIEF DESCRIPTION OF THE DRAWINGS

The appended figures depict certain aspects of the one or more embodiments of the present disclosure and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
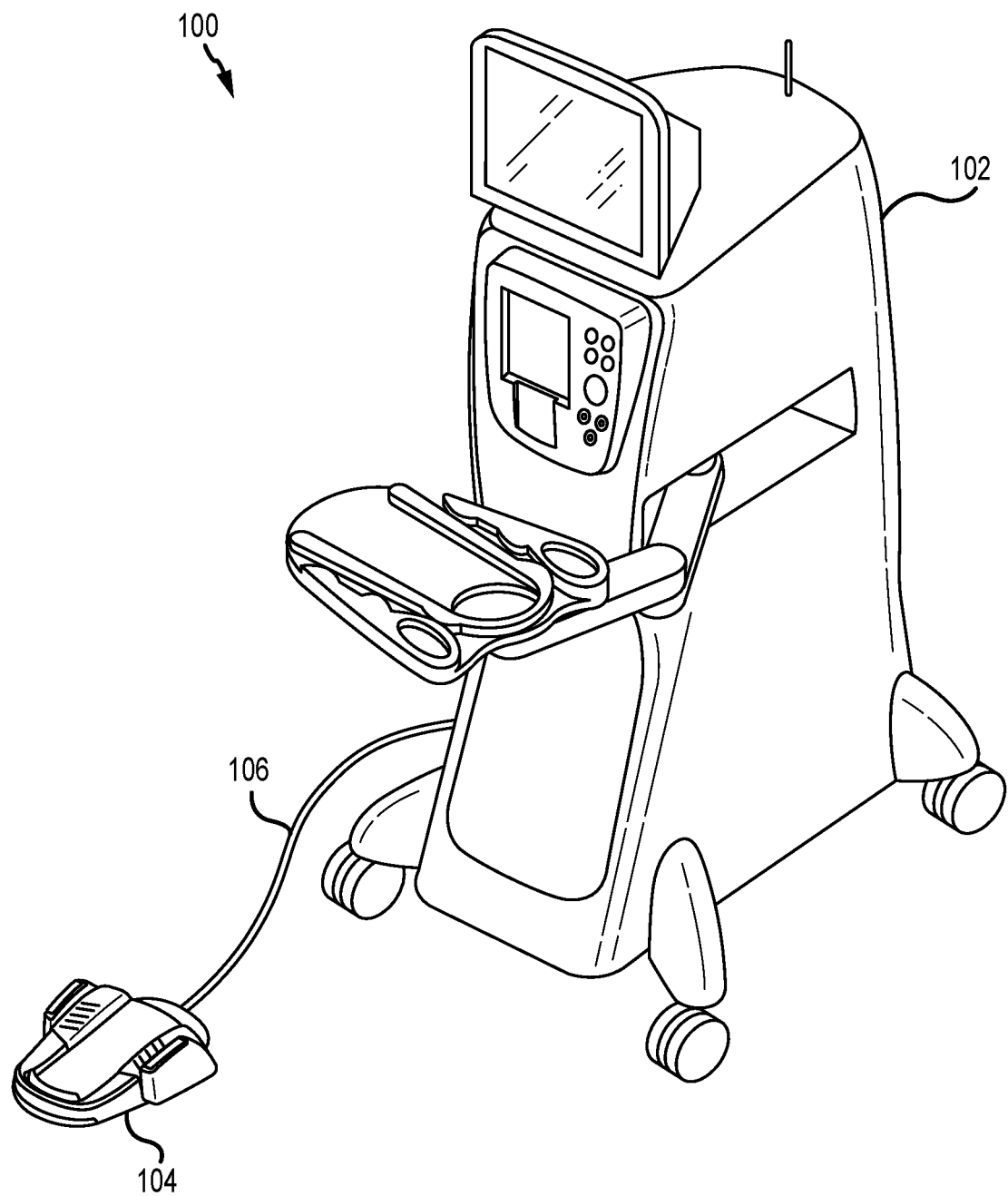
FIG. 1 is a perspective view of a surgical system comprising a footswitch in accordance with a particular embodiment of the present disclosure.

In accordance with the teachings of the present disclosure, a surgical footswitch comprising at least one elevated, auxiliary button is disclosed. In a particular embodiment, the surgical footswitch comprises a footswitch base, a treadle mounted on the footswitch base, a first primary button positioned on an upper surface of the footswitch base along a first lateral side of the treadle, a first auxiliary button housing positioned along a lateral side of the first primary button opposite the treadle, and a first auxiliary button mounted on an upper surface of the first auxiliary button housing, wherein an upper surface of the first auxiliary button is elevated in relation to an upper surface of the first primary button.

In another embodiment, the surgical footswitch comprises a footswitch base, a treadle mounted on the footswitch base, a first primary button positioned on an upper surface of the footswitch base along a first lateral side of the treadle, and a second primary button positioned on the upper surface of the footswitch base along a second lateral side of the treadle. The exemplary footswitch further comprises a first auxiliary button housing positioned along a lateral side of the first primary button opposite the treadle, a first auxiliary button mounted on an upper surface of the first auxiliary button housing, a second auxiliary button housing positioned along a lateral side of the second primary button opposite the treadle, and a second primary button mounted on an upper surface of the second auxiliary button housing. An upper surface of the first auxiliary button may be elevated in relation to an upper surface of the first primary button, and an upper surface of the second auxiliary button may be elevated in relation to an upper surface of the second primary button.

By providing one or more elevated, auxiliary buttons, particular embodiments of the present disclosure are able to provide users with a surgical footswitch that offers enhanced functionality. For example, a user may be able to select between more functions, or combinations of functions, due to the addition of the auxiliary buttons, without removing his or her foot from the treadle. Moreover, by elevating the auxiliary buttons relative to the primary buttons, particular embodiments may help reduce the risk that the user will inadvertently activate the auxiliary buttons when attempting to activate the primary buttons and/or treadle of the footswitch. Similarly, particular embodiments may also help to reduce the risk that the user will inadvertently activate the primary buttons and/or treadle when attempting to activate the auxiliary buttons. And, by placing the auxiliary buttons such that there is a significant difference in the vertical and/or horizontal placement of the auxiliary and primary buttons, particular embodiments may better enable the user to activate the buttons without having to view the footswitch, allowing the user to maintain his or her vision on the surgical field.

FIG. 1 illustrates a surgical system 100 in accordance with a particular embodiment of the present disclosure. As shown in FIG. 1, surgical system 100 comprises a surgical console 102, a surgical footswitch 104, and a cable 106 coupling surgical footswitch 104 to surgical console 102. Surgical console 102 may be any console used for a number of different surgeries, including but not limited to ophthalmic surgery. For example, surgical console 102 may be a console used for cataract surgery (such as the CENTURION® Vision System sold by Alcon Vision, LLC of Fort Worth, Tex.) or a console use for vitreoretinal surgery (such as the CONSTELLATION® Vision System, also sold by Alcon Vision, LLC). Surgical footswitch 104 may be used to control various functions of surgical console 102, such as activating various features and/or controlling certain parameters of the console's operation, by sending various commands to the console over cable 106. That said, although surgical system 100 is illustrated as including cable 106, the connection between the surgical console 102 and the surgical footswitch 104 may be accomplished by any variety of methods that would be known to a person of skill in the art including physical connections and wireless connections. As will be discussed in more detail below, the activation of the various functions and/or selection of the various parameters of the console's operation may be accomplished using a treadle (or pedal) and/or one or more buttons located on footswitch 104.

Figure 2A:
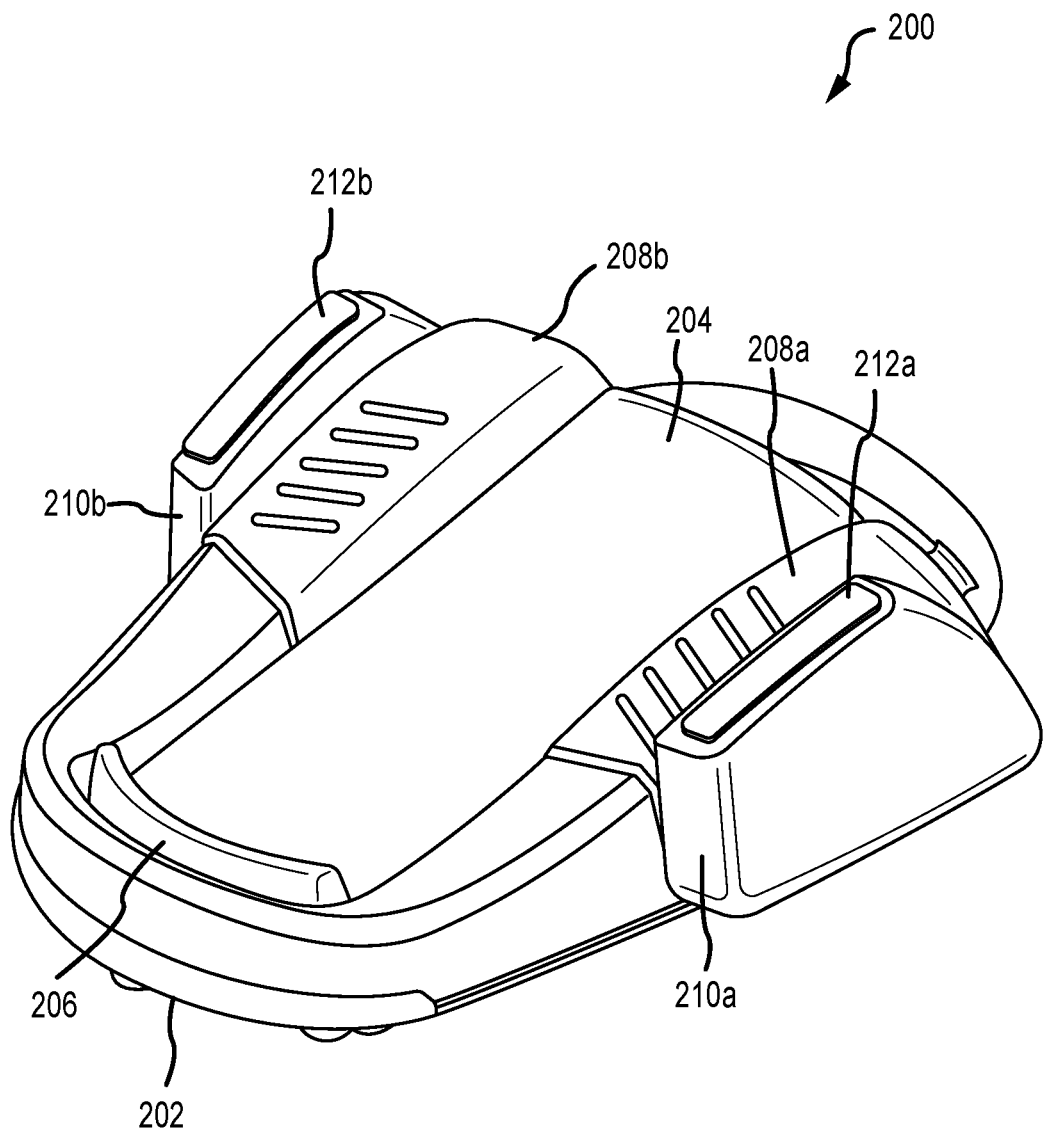
FIG. 2A is a perspective view of a footswitch in accordance with a particular embodiment of the present disclosure.

FIG. 2A shows a perspective view of a surgical footswitch 200 in accordance with a particular embodiment of the present disclosure. As shown in FIG. 2A, surgical footswitch 200 comprises a base 202 and a treadle 204 mounted thereon. In particular embodiments, treadle 204 may comprise a heel cup 206, which serves to cradle the proximal end (e.g., heel) of a user's foot during operation. In particular embodiments, heel cup may also incorporate one or more switches for activating functions of a surgical console. In general, treadle 204 may be depressed and/or released like an accelerator pedal to activate various functions of the surgical console.

Surgical footswitch 200 may also include one or more primary buttons 208 along one or both lateral sides of the treadle 204 for operating various functions of the surgical console 102. As shown in FIG. 2A, footswitch 200 includes two such primary buttons—primary button 208a on the right side of treadle 204 and primary button 208b on the left side of treadle 204. In particular embodiments, these primary buttons 208 may be mounted on footswitch 200 such that they are located near the distal end of a user's foot during operation. However, primary buttons 208 may be located closer to the proximal end of the user's foot, as well. In particular embodiments, these primary buttons 208 may be elevated relative to treadle 204 to reduce the risk of a user inadvertently activating one of the primary buttons 208 when depressing/releasing treadle 204.

Surgical footswitch 200 also comprises one or more auxiliary buttons 212 located lateral of primary buttons 208, opposite treadle 204. For example, as illustrated in FIG. 2A, footswitch 200 includes an auxiliary button 212a on the right side of primary button 208a and an auxiliary button 212b on the left side of primary button 208b. Similar to primary buttons 208, auxiliary buttons 212 may be elevated relative to treadle 204 to reduce the risk of a user inadvertently activating one of the auxiliary buttons 212 when depressing/releasing treadle 204. Auxiliary buttons 212 may also be elevated relative to primary buttons 208 to reduce the risk of a user inadvertently activating one of the primary buttons 208 when attempting to activate one of the auxiliary buttons 212, and/or vice versa. In particular embodiments, these auxiliary buttons 212 may be mounted on footswitch 200 such that they are located near the distal end of a user's foot during operation, although they may also be located closer to the proximal end of the user's foot.

Accordingly, as shown in FIG. 2A, auxiliary buttons 212 are mounted on auxiliary button housings 210 located on the lateral sides of footswitch 200. For example, auxiliary button 212a is mounted on auxiliary button housing 210a on the right side or primary button 208a, and auxiliary button 212b is mounted on auxiliary housing 210b on the left side of primary button 208b. In particular embodiments, auxiliary button housings 210 rise vertically above the level of the treadle 204 and provide a physical separation that allows a user to differentiate between the primary buttons 208 and the auxiliary buttons 212 using the distal portion of his or her foot. In particular embodiments, this allows a user to activate primary buttons 208 and/or auxiliary buttons 212 on surgical footswitch 200, without raising or removing (or by minimally displacing) his or her heel from heel cup 206. This may be especially advantageous because translation of the user's foot during surgical procedures may be undesirable because such movement may cause the user's upper body to also move, potentially affecting the user's hand position. Also, the user may have to look directly at the surgical footswitch, rather than at the surgical field, to properly reposition his or her foot into the correct position on treadle. That said, although it may be advantageous for a user to be able activate the primary buttons 208 and auxiliary buttons 212 located on the surgical footswitch 200 by sweeping the distal end of his or her foot across the various buttons without much, if any, movement of the heel portion of his or her foot, the teachings of the present disclosure do not require that the heel portion of the user's foot remain planted within the heel cup. Other embodiments of the present disclosure may allow the user to translate either or both of the distal and heel portions of his or her foot after which the foot may be returned to its original position on treadle 204.

In particular embodiments, the size, shape, and configuration of auxiliary button housings 210 may be selected to provide a significant difference in height between primary buttons 208 and auxiliary buttons 212. For example, a user rotating the distal end of his or her foot across the footswitch 200 may feel the interior side of auxiliary button housing 210, and know to raise and continue to rotate the distal end of that foot further to access auxiliary button 212 on top of the housing 210, or to simply press down to activate primary button 208, if that is desired. Accordingly, in particular embodiments, primary buttons 208 and auxiliary buttons 212 may be operated by touch with minimal effect on the user's upper body and without requiring the user to directly view footswitch 200, allowing the user to maintain his or her vision on the surgical field.

The size, shape, and configuration of auxiliary button housings 210, including their placement relative to the other components of footswitch 200, may also be determined by a number of other factors. For example, in particular embodiments, the size, shape, and placement of auxiliary button housings 210 may be selected to provide vertical and horizontal separation of the top plane of the housing 210 from the top plane of primary button 208 sufficient to prevent and/or reduce the risk a user will unintentionally activate primary button 208 when attempting to activate auxiliary button 212. Similarly, the vertical and horizontal separation between auxiliary button housing 210 and primary button 208 may also be selected such that both primary button 208 and auxiliary button 212 may be comfortably accessed using the distal end of the user's foot without removing his or her heel from the heel cup 206. And, the volume necessary to enclose the switching mechanism associated with auxiliary button 212, to properly support auxiliary button 212, and to properly attach auxiliary button 212 to surgical footswitch 200 may also affect the size, shape, and configuration of auxiliary button housings 210. Other design considerations may also be apparent to one of ordinary skill in the art with the benefit of this disclosure.

In particular embodiments of the present disclosure, the vertical separation between the top plane of the auxiliary button housing 210 and the top plane of the primary button 208 may be selected to be at least 10 mm (millimeters), so as to allow a user to readily distinguish between the primary button 208 and the auxiliary button 212 without viewing footswitch 200. Similarly, in particular embodiments, the vertical separation between the top plane of auxiliary button housing 210 and primary button 208 may be selected not to exceed 50 mm, so that the primary button 208 and auxiliary button 212 may be activated by a user without significantly shifting his or her foot and/or removing his or her heal from heal cup 206. That said, other amounts of vertical separation are also possible within the teachings of present disclosure, depending on the intended use of the footswitch and the size of the foot of the intended user.

Primary buttons 208 and auxiliary buttons 212 may also have different shapes and/or orientations within the teachings of the present disclosure. For example, in particular embodiments, the top surfaces of the buttons may differ in angle and orientation to each other. Furthermore, the surfaces of the primary button 208, auxiliary button 212 and/or auxiliary button housing 210 are not required to be planar and, in particular embodiments, may be curved, pyramidal, prismatic, or any other suitable surface type.

Figure 2B:
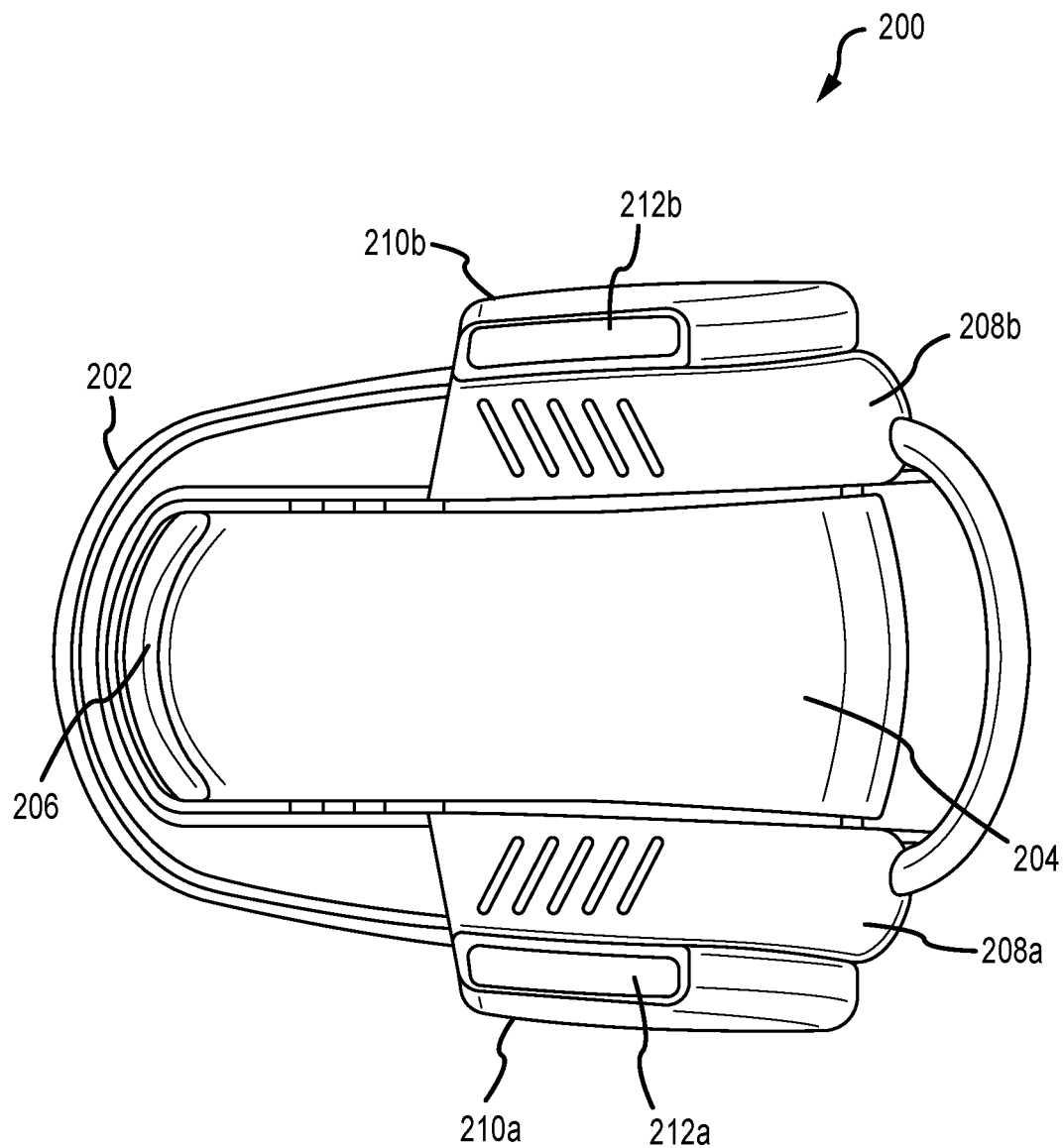
FIG. 2B is a top view of the footswitch illustrated in FIG. 2A.

FIG. 2B shows a top view of footswitch 200, better illustrating the horizontal placement of, and separation between, treadle 204, primary buttons 208a and 208b, and auxiliary buttons 212a and 212b. As shown in FIG. 2B, primary buttons 208a and 208b are located adjacent to treadle 204, with primary button 208a on the right side of treadle 204 and primary button 208b on the left side of treadle 204. Moreover, primary buttons 208a and 208b are located towards the distal end of treadle 204 (i.e., away from heel cup 206), allowing them to be more easily activated using the distal end of a user's foot. Auxiliary button housings 210a and 210b are located adjacent to primary buttons 208a and 208b, respectively, on the exterior sides of the primary buttons 208, opposite treadle 204. Auxiliary buttons 212a and 212b are mounted on top of auxiliary button housing 210a and 210b, respectively. Like primary buttons 208a and 208b, auxiliary buttons 212a and 212b are also located towards the distal end of treadle 204. In particular embodiments, primary buttons 208a and 208b and auxiliary buttons 212a and 212b are positioned such that a user may be able to rotate his or her foot and activate the buttons 208 and 212 using the distal end of his or her foot without removing his or her heel from heel cup 206.

Figure 2C:
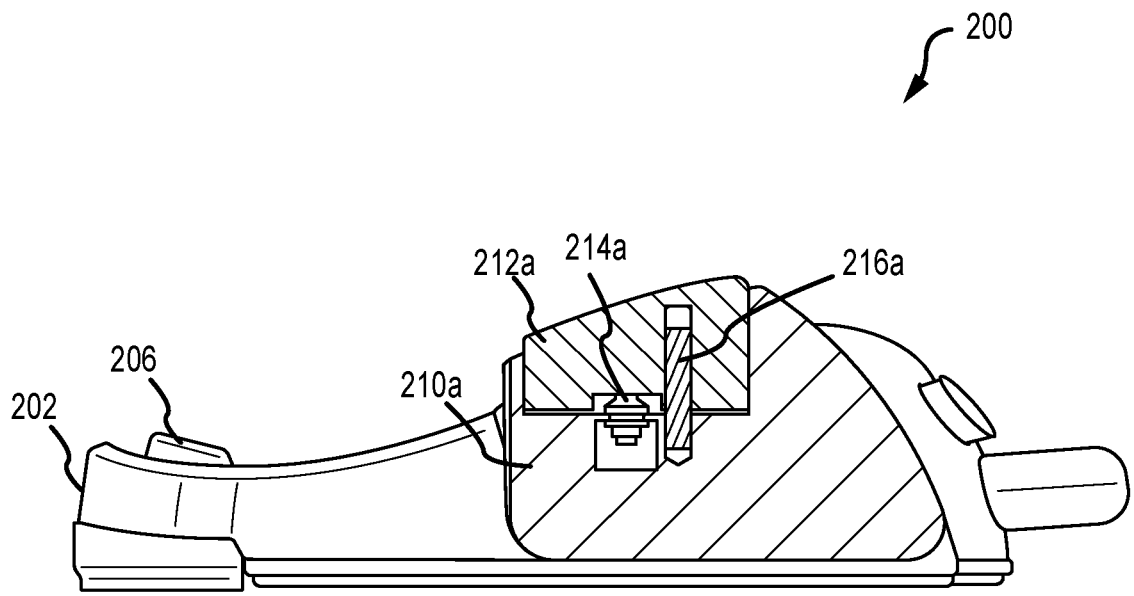
FIG. 2C is a partial cross-sectional view of the footswitch illustrated in FIGS. 2A-B viewed from the side.

FIG. 2C illustrates a cutaway side view of footswitch 200, showing the interior of auxiliary button 212a and auxiliary button housing 210a in accordance with a particular embodiment of the present disclosure. In this particular embodiment, auxiliary button 212a interfaces with a single, vertically activated switch 214a located within auxiliary button housing 210a to control one or more functions of a surgical console.

When auxiliary button 212a is depressed by the user's foot, it interfaces with the spring-loaded switch 214a to engage the switch 214a, by bringing two sections of the internal electrical switch into electrical contact with each other. The spring contained within the spring-loaded switch 214a provides the force necessary to resist both the force of gravity and provide resistance to the force exerted by the user's foot depressing the auxiliary button 212a and only allow engagement of the spring-loaded switch 214a when desired by the user. Because the auxiliary button is configured to move in the vertical direction, but may also experience forces, torques, and moments in other directions, particular embodiments of the present disclosure employ, an alignment pin 216a to maintain the correct vertical alignment of, and prevent the jamming of, auxiliary button 212a while the button 212a is in the process of being depressed by the user's foot. Similarly, the auxiliary button housing 210a may also serve to constrain the lateral movement of auxiliary button 212a. Auxiliary button housing 210b and auxiliary button 212b may also utilize a similar alignment pin and switch configuration (not illustrated).

In addition, although switch 214a has been described as a spring-loaded switch, other types of switches, including both mechanical and electronic switches, may be used within the teachings of the present disclosure. For example, suitable mechanical switches include, but are not limited to, single pole single throw switches (SPST); single pole double throw switches (SPDT); double pole single throw switches (DPST); double pole double throw switches (DPDT); push button switches; toggle switches; limit switches; float switches; flow switches; and pressure switches. Suitable electronic switches may include, but are not limited to, bipolar transistors; power diodes; metal-oxide-semiconductor field-effect transistors (MOSFET); insulated-gate bipolar transistors (IGBT); silicon controlled rectifiers (SCR); triodes for alternating current (TRIAC); diodes for alternating current (DIAC); and gate turn-off thyristors (GTO).

Each of the switches contained within the surgical footswitch 200 are connected to electrical circuits which may, in turn, be connected to a surgical console (e.g., surgical console 102 in FIG. 1) via any suitable connection (e.g., cable 106 in FIG. 1), including, but not limited to, a direct cable connection, a fiber optic link, and/or a wireless connection. Through this connection, the switches may be used to control various functions of the surgical console. Some functionalities of the surgical console may be controlled via a simple on-or-off switch (e.g., spring-loaded switch 214a). However, other functionalities may require one of the more complex switches discussed above, such as a pressure sensing switch, or multiple position switch. In particular embodiments, the switches may also provide feedback to the surgeon regarding activation via resistance to depression, sounds, clicking or a visual indicator. For example, in particular embodiments, the switches may provide haptic feedback. This feedback can be established through the connection between the surgical console (e.g., surgical console 102 in FIG. 1) and the surgical footswitch 200, and may be one or more of a variety of signals including, but not limited to, an increase in resistance to depression for the switch, vibration upon activation/deactivation, and/or emittance of a sounds upon activation/deactivation. The choice of the particular type of switch used may be based upon the desired functionality of the surgical console associated with the footswitch 200.

Figure 2D:
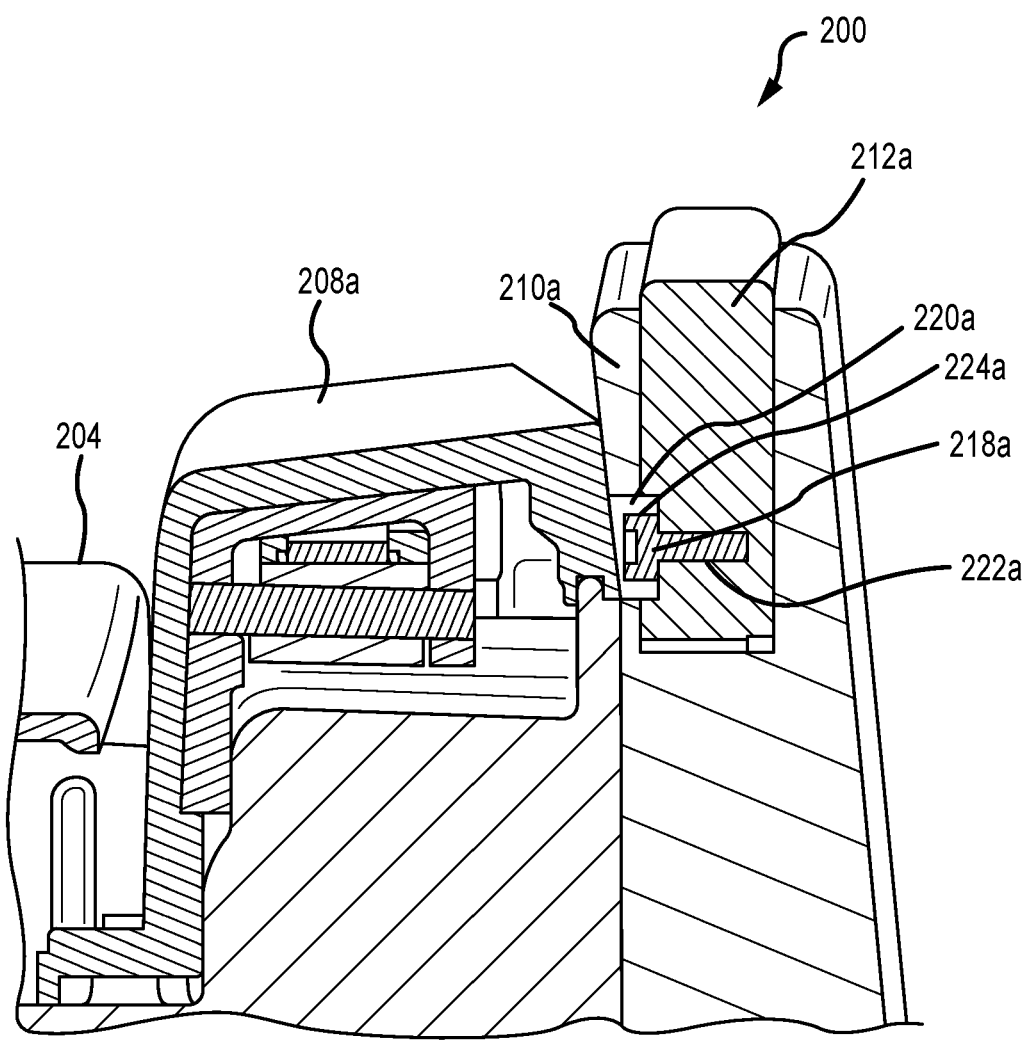
FIG. 2D is a partial cross-sectional view of the footswitch illustrated in FIGS. 2A-C viewed from the proximal end of the footswitch.

FIG. 2D shows partial cross-sectional view of footswitch 200, viewed from the proximal end of the footswitch (i.e., orthogonal to the view in FIG. 2C). In particular, FIG. 2D shows the mechanism that retains auxiliary button 212a within the auxiliary button housing 210a in particular embodiments of the present disclosure. Auxiliary button housing 210a contains a cavity 220a orientated parallel to the direction of travel for auxiliary button 212a. Auxiliary button 212a contains a shaft 222a into which a screw 218a can be driven. As illustrated screw 218a may be a socket head screw, although other types of screws and fasteners are possible within the teachings of the present disclosure. Cavity 220a is sized to allow the screwhead 224a of screw 218a to slide vertically within the cavity. In particular embodiments, the vertical length of cavity, parallel to the direction of travel for auxiliary button 212a, is chosen to allow button 212a to be depressed sufficiently to activate spring-loaded switch 214a (FIG. 2C) and to also retain button 212a at the top of the travel of the spring-loaded switch 214a, to prevent the button 212a from escaping auxiliary button housing 210a.

Generally, each of the components of surgical footswitch 200 elements described above may be made of a variety of plastics or metals, such as stainless steel or titanium, that are in common use within the industry. Moreover, although footswitch 200 has been illustrated and described as having a single auxiliary button 212 mounted on each auxiliary button housing 210, in particular embodiments of the present disclosure, multiple auxiliary buttons 212 may be mounted on an individual auxiliary button housing 210 to provide additional control options to the user of footswitch 200.

Accordingly, by placing elevated auxiliary buttons alongside the primary buttons of a surgical footswitch, particular embodiments of the present disclosure are able to provide a surgical footswitch that offers enhanced functionality. For example, a user may be able to select between more functions, or combinations of functions, due to the addition of the auxiliary buttons, without removing his or her foot from the treadle. Moreover, based on the horizontal and vertical placement of the auxiliary buttons relative to the primary buttons and treadle of the footswitch, particular embodiments may also reduce the risk of a user inadvertently or mistakenly activating a button other than the one desired.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A surgical footswitch comprising:
   a footswitch base;
   a treadle mounted on the footswitch base, wherein the treadle comprises a heel cup directly attached to the treadle;
   a first primary button positioned on an upper surface of the footswitch base along a first lateral side of the treadle and extending along a first length of the treadle;
   a first auxiliary button housing positioned along a lateral side of the first primary button, opposite the first length of the treadle;
   a first auxiliary button mounted on an upper surface of the first auxiliary button housing, wherein an upper surface of the first primary button is sloped upwards from a lower height adjacent the treadle to a higher height adjacent the first auxiliary button and an upper surface of the first auxiliary button is sloped upward from a lower height at a point on the first auxiliary button closest to the heel cup to a higher height at a point on the first auxiliary button most remote from the heel cup;
   wherein the treadle is configured to activate a first function of a surgical console, the first primary button is configured to activate a second function of the surgical console, and the first auxiliary button is configured to activate a third function of the surgical console;
   wherein the upper surface of the first auxiliary button is elevated in relation to the upper surface of the first primary button; and
   wherein a proximal end of the first primary button is situated closer to the heel cup than to a distal end of the treadle most remote from the heel cup, wherein the proximal end of the first primary button is situated closer to the heel cup than a proximal end of the first auxiliary button is situated in relation to the heel cup, wherein the proximal end of the first auxiliary button is situated closer to the heel cup than to the distal end of the treadle most remote from the heel cup, and wherein a distal end of the first primary button is situated closer to the distal end of the treadle than a distal end of the first auxiliary button is situated in relation to the distal end of the treadle.

2. The surgical footswitch of claim 1, further comprising:
a second primary button positioned on the upper surface of the footswitch base along a second lateral side of the treadle;
wherein the second primary button is configured to activate a fifth function of the surgical console; and
wherein the first lateral side of the treadle is opposite the second lateral side of the treadle.

3. The surgical footswitch of claim 2, further comprising:
a second auxiliary button housing positioned along a lateral side of the second primary button, opposite the treadle; and
a second auxiliary button mounted on an upper surface of the second auxiliary button housing;
wherein the second auxiliary button is configured to activate a sixth function of the surgical console; and
wherein an upper surface of the second auxiliary button is elevated in relation to an upper surface of the second primary button.

4. The surgical footswitch of claim 1, further comprising:
a second auxiliary button mounted on the upper surface of the first auxiliary button housing;
wherein the second auxiliary button is configured to activate a fifth function of the surgical console.

5. The surgical footswitch of claim 1, wherein a difference in elevation between the upper surface of the first auxiliary button and the upper surface of the first primary button is less than 50 millimeters.

6. The surgical footswitch of claim 1, wherein a difference in elevation between the upper surface of the first auxiliary button and the upper surface of the first primary button is between 10 millimeters and 50 millimeters.

7. The surgical footswitch of claim 1, wherein the first primary button is positioned such that a user may activate the first primary button by depressing the first primary button.

8. The surgical footswitch of claim 1, wherein the first auxiliary button is positioned such that a user may activate the first auxiliary button by depressing the first auxiliary button.

9. The surgical footswitch of claim 1, wherein the first auxiliary button housing is integrated into the footswitch base.

10. The surgical footswitch of claim 1, wherein at least one of the first primary button, the second primary button, the first auxiliary button, and the second auxiliary button is configured to provide feedback upon activation via at least one of a resistance to depression, a vibration, a sound indicator, and a visual indicator.

11. A surgical footswitch comprising:
a footswitch base;
a treadle mounted on the footswitch base, wherein the treadle comprises a heel cup directly attached to the treadle;
a first primary button positioned on an upper surface of the footswitch base along a first lateral side of the treadle and extending along a first length of the treadle;
a second primary button positioned on the upper surface of the footswitch base along a second lateral side of the treadle;
a first auxiliary button housing positioned along a lateral side of the first primary button, opposite the first length of the treadle;
a first auxiliary button mounted on an upper surface of the first auxiliary button housing, wherein an upper surface of the first primary button is sloped upwards from a lower height adjacent the treadle to a higher height adjacent the first auxiliary button and an upper surface of the first auxiliary button is sloped upward from a lower height at a point on the first auxiliary button closest to the heel cup to a higher height at a point on the first auxiliary button most remote from the heel cup;
a second auxiliary button housing positioned along a lateral side of the second primary button, opposite the treadle;
a second auxiliary button mounted on an upper surface of the second auxiliary button housing;
wherein the treadle is configured to activate a first function of a surgical console, the first primary button is configured to activate a second function of the surgical console, the second primary button is configured to activate a third function of the surgical console, the first auxiliary button is configured to activate a fourth function of the surgical console, and the second auxiliary button is configured to activate a fifth function of the surgical console;
wherein the upper surface of the first auxiliary button is elevated in relation to the upper surface of the first primary button, wherein a proximal end of the first primary button is situated closer to the heel cup than a proximal end of the first auxiliary button is situated in relation to the heel cup, and wherein a distal end of the first primary button is situated closer to a distal end of the treadle than a distal end of the first auxiliary button is situated in relation to the distal end of the treadle;
wherein an upper surface of the second auxiliary button is elevated in relation to an upper surface of the second primary button, wherein a proximal end of the second primary button is situated closer to the heel cup than a proximal end of the second auxiliary button is situated in relation to the heel cup, and wherein a distal end of the second primary button is situated closer to a distal end of the treadle than a distal end of the second auxiliary button is situated in relation to the distal end of the treadle; and
wherein the proximal end of the first primary button is situated closer to the heel cup than to a distal end of the treadle most remote from the heel cup, and the proximal end of the first auxiliary button is situated closer to the heel cup than to the distal end of the treadle most remote from the heel cup.

12. The surgical footswitch of claim 11, wherein a difference in elevation between the upper surface of the second auxiliary button and the upper surface of the second primary button is at least 10 millimeters.

13. The surgical footswitch of claim 11, wherein a difference in elevation between the upper surface of the first auxiliary button and the upper surface of the first primary button is less than 50 millimeters.

14. The surgical footswitch of claim 11, wherein a difference in elevation between the upper surface of the second auxiliary button and the upper surface of the second primary button is less than 50 millimeters.

15. The surgical footswitch of claim 11, wherein a difference in elevation between the upper surface of the first auxiliary button and the upper surface of the first primary button is between 10 millimeters and 50 millimeters.

16. The surgical footswitch of claim 11, wherein a difference in elevation between the upper surface of the second auxiliary button and the upper surface of the second primary button is between 10 millimeters and 50 millimeters.

17. The surgical footswitch of claim 11, wherein the first auxiliary button is positioned such that a user may activate the first auxiliary button by depressing the first auxiliary button.

18. The surgical footswitch of claim 17, wherein the second auxiliary button is positioned such that the user may activate the second auxiliary button.

19. The surgical footswitch of claim 11, wherein the first and second auxiliary button housings are integrated into the footswitch base.

20. The surgical footswitch of claim 11, wherein at least one of the first primary button, the second primary button, the first auxiliary button, and the second auxiliary button is configured to provide feedback upon activation via at least one of a resistance to depression, a vibration, a sound indicator, and a visual indicator.

* * * * *